United States Patent [19]

Winicki

[11] 4,067,329
[45] Jan. 10, 1978

[54] TUBE DISCONNECTION WARNING DEVICE

[75] Inventor: Bernard Winicki, Neuilly sur Seine, France

[73] Assignee: Union Chimique Continentale-U.C.C., Puteaux, France

[21] Appl. No.: 647,199

[22] Filed: Jan. 7, 1976

[30] Foreign Application Priority Data

Jan. 17, 1975  France ................................ 75.01398

[51] Int. Cl.² ............................................ A61M 16/00
[52] U.S. Cl. .................................. 128/145.8; 128/203;
128/351; 137/557; 137/840; 340/242; 285/249;
285/93
[58] Field of Search ............... 128/145.8, 145.6, 145.5,
128/142, 142.2, 188, 203, 351, 208; 340/242,
241, 240, 239, 279; 137/557, 840; 285/249, 93

[56] References Cited

U.S. PATENT DOCUMENTS 1,150,204  8/1915  Julian ................................... 340/240
2,151,092  3/1939  Dunsheath .......................... 340/242
3,952,740  4/1976  Scurlock ............................ 128/145.8

Primary Examiner—Robert W. Michell
Assistant Examiner—Henry J. Recla

[57] ABSTRACT

A warning device of the disconnection of a tube from another tube, for example, of a respirator canula from a patient's medical equipment comprises: a source of gas under pressure; a pneumatic switch; a filter; an adjustable pressure reducing valve; and a pneumatic cell of the fully open — fully closed type, supplied by said pressure-reducing valve. A sensing tube terminates in at least one orifice between the walls in contact of two said tubes when they are normally connected and controls the cell. A distributor is supplied by said pressure-reducing valve and controlled at its resting input and at its working input by the cell. At least one alarm means is supplied by the distributor. The said orifice may be an open end of said sensing tube, inserted between the walls in contact of the canula and of the apparatus of the patient.

11 Claims, 7 Drawing Figures

TUBE DISCONNECTION WARNING DEVICE

BACKGROUND OF THE INVENTION

1. Field of the Invention

The present invention relates to a warning device giving a warning in the event of the disconnection of a tube. More particularly it relates to a warning device giving an optical and/or sound and/or light signal or the like in the event of the disconnection of a tube and more especially the disconnection of a tube connected to the canula of a respirator.

The importance of such a warning device is obvious : in the case of a respirator such a disconnection could result in the asphyxia and death of a patient.

2. Description of the Prior Art

Previously known warning devices of the disconnection of a tube and notably, in the case of disconnection between the air supply to a respirator and the endotracheal probe in the intensive care unit of a hospital, are constituted by electrical circuits which emit a warning signal either by the action of a pressure-gauged overpressure, or due to variations in the volume of the ventilation air, or under the effect of variations in the air temperature, or under the effect of variations in the compliance of the thoracic cage, or in the case of the cessation of air flow in the ventilating circuit.

Such known apparatuses have the common drawback of being constituted by electrical circuits which have dangers due to switch sparks and to electrical shocks which can occur; in addition the operation of such known apparatus is not reliable.

OBJECTS AND SUMMARY OF THE INVENTION

It is an object of the present invention to provide an apparatus giving warning in the case of disconnection of a tube, particularly of a respirator, which responds better to the requirements of practice than previously known devices for the same purpose.

It is also an object of the invention to provide a warning device which is not electrical but pneumatic.

It is another object of the invention to provide a pneumatic warning device which is light and not cumbersome, so as to be easily located near the bed of a patient, in a clinic and in an ambulance.

It is a further object to provide a warning device which can be supplied by the source (air and/or oxygen) for the respirator.

It is another object to provide a warning device which can operate in a caisson under pressure.

Another object of the invention is to provide a warning device which is positive and reliable and, in particular, eliminates any risk of contamination from one patient to another and whose sensing tube is pressurised to prevent its clogging by tracheal secretions of the patient.

Accordingly, to respond to one or more of these requirements and desiderata, according to the present invention there is provided a tube disconnection warning device comprising in combination, starting from an independant source or from the source of the respirator, a pneumatic switch, a filter, an adjustable pressure-reducing valve, a pneumatic cell of the fully open — fully closed type, supplied through said pressure-reducing valve, controlled by a sensing tube which is supplied by said pneumatic cell, and which supplies, responsive to the pressure in said sensing tube, either the resting input or the working input of a distributor, supplied by said pressure-reducing valve and supplying, in working position, a pneumatic display and/or a sounding device and/or a pneumoelectric relay, said sensing tube terminating at an open end, inserted between the walls of a conventional canula and of the equipment of the patient, or connected to a tube added to a normal or T or Y canula leading to the place or places to be monitored.

BRIEF DESCRIPTION OF THE DRAWINGS

The invention will be better understood from the description which follows, with reference to the accompanying drawing, in which.

It must be well understood, however, that the aforementioned drawing and the corresponding description are given purely by way of illustration and do not constitute any limitation of the invention.

DESCRIPTION OF PREFERRED EMBODIMENTS

Figure 1:
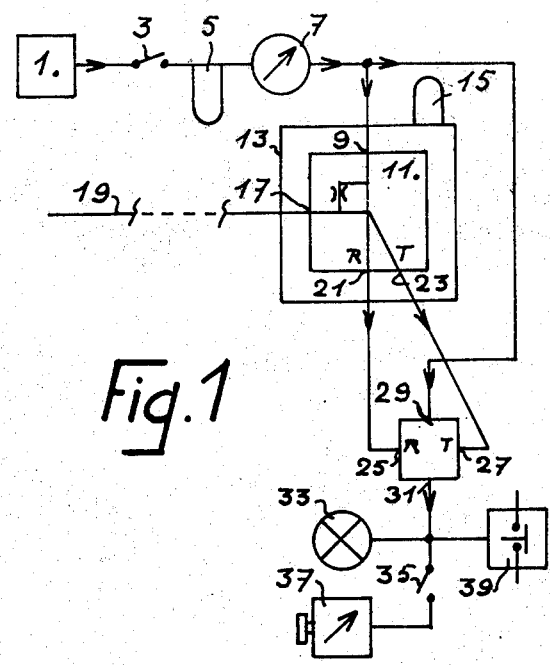
FIG. 1 is a functional diagram of the warning device according to the invention.

The funtional diagram of a warning device according to the invention will first be described with reference to FIG. 1.

The source 1 of gas (air or oxygen) under pressure, for example 3 kg/cm$^2$, may be, as desired or opportune, the source of a respirator, or a wall connector for oxygen or compressed air or an auxiliary gas reserve for installation in a vehicle, for example. The source 1 supplies, in series, a switch 3, a filter 5, and an adjustable pressure-reducing valve 7, which may, for example, be of the "Mini-Quiet" type marketed by the CLIMAX-FRANCE Company. The adjustable pressurereducing valve 7 supplies, at the pressure of about 0.3 kg/cm$^2$, the input 9 of a pneumatic cell 11 of the fully open or fully closed type, which may, for example, be of the type marketed by the SOVCOR-AUTOMATISMES Company. The pneumatic cell 11 is preferably housed in a fluid-tight box 13 provided with a silencer 15 so as to reduce the noise due to the gas exhaust. The control orifice 17 of the pneumatic cell 11 is provided with a sensing tube 19 supplied through the pneumatic cell 11 in the presence of pressure at the control orifice 17; the pneumatic cell 11 connects its input 9 to a rest output 21, and in the absence of said pressure, it connects its input 9 to a work output 23. These two outputs are respectively connected to two homologous inputs 25 and 27 of a distributor 29 supplied by the adjustable pressure-reducing valve 7. The distributor 29, in working position, supplies is output 31, which is connected to a pneumatic display 33, and/or to a switch 35 followed by a sound apparatus 37 such as a whistle or a siren with adjustable sound volume or horn-type klaxon and/or a pneumo-electrical relay 39 for a luminous display and-/or distant alarm.

It will be noted that the two positions, resting and working, of the pneumatic cell 11, and those of the distributor 29, are positively controlled, in order to increase the safety and reliability of the apparatus.

Figure 2:
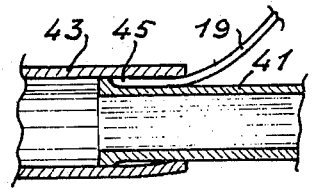
FIG. 2 shows, in section, the manner in which a conventional canula can house a sensor for the alarm device according to the invention.

The sensing tube 19 is a flexible tube, of 1 to 2 mm internal diameter, connected to the canula of the respirator as described below. FIG. 2 shows, in section, a conventional canula 41, in position in the respirator 43. The sensing tube 19 ends at an open end 45, inserted between the walls of the canula 41 and the apparatus 43 of the patient. It is clear that the detachment of the canula, or disconnection from the patient, opens the sensing tube 19, which causes the pneumatic cell 11 and the distributor 29 to rock into their working positions, which sets off the alarm 33 – 37 – 39.

Figure 3:
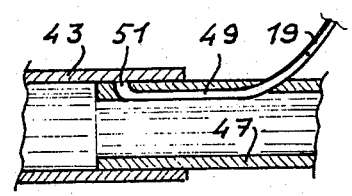
FIG. 3 shows, in section, a canula modified to house a sensor for the alarm device according to the invention.

FIG. 3 shows, in section, a canula 47, modified by the addition of a tube 49, connected externally to the sensing tube 19. The other end 51 of the tube 49 opens at the outer surface of the canula 47 against the inner surface of the apparatus 43 of the patient. The operation is identical with that described with regard to FIG. 2.

Figure 4:
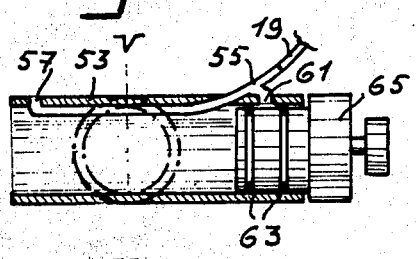
FIGS. 4 and 5 are right-angled cross-sections, FIG. 4 along the line IV—IV of FIG. 5, and FIG. 5 along the line V—V of FIG. 4, of a T-shaped canula adapted for housing a sensor for the alarm device according to the invention.
Figure 5:
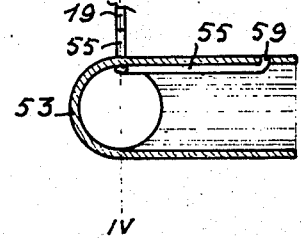

FIGS. 4 and 5 are two right-angled cross-sections of a T canula 53, modified by the addition of a tube 55, connected externally to the sensing tube 19. The tube 55 comprises three orifices 57, 59, 61; the orifice 57 opens at the outer surface of the canula 53 against the inner surface of the apparatus of the patient (not shown); the orifice 59 opens at the outer surface of the canula 53 against the inner surface of the tube of the respirator (not shown); the orifice 61 opens at the inner surface of the canula 53 between two toric seals 63 of the stopper 65 through which the doctor draws off the tracheal secretions. Each of these three orifices triggers, by its opening, the operation described with respect to FIG. 2.

Figure 6:
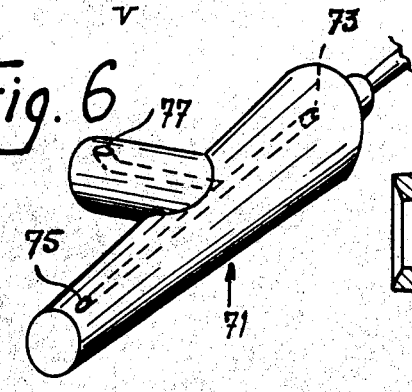
FIG. 6 is a perspective view of another embodiment showing the association of the canula and the sensor for a warning device according to the invention.
Figure 7:
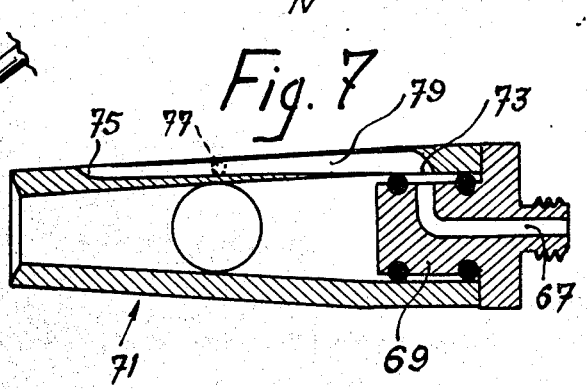
FIG. 7 is a longitudinal sectional view of the embodiment of FIG. 6.

FIGS. 6 and 7 show another embodiment of the association of a T canula and of the sensing tube, in which the input from the sensing tube 67 is effected in the stopper 69 of the T canula 71 modified by the addition of a tube 79 connected at its end 73 to the inner end of the sensing tube 67 whilst its orifice 75 opens at the outer surface of the canula 71 against the inner surface of the apparatus (not shown) of the patient and its orifice 77 opens at the outer surface of the canula 71, against the inner surface of the tube of the respirator (not shown). Such an embodiment has the advantage of enabling the doctor to aspirate in the canula without having to clamp the tube of the sensor to avoid triggering the alarm, provided that the stopper 69 is placed in a tube fixed on the apparatus, so as to obturate the orifice of the stopper.

The warning device according to the invention consumes about 10% (0.5 l/min) of the consumption of a respirator operating normally : hence there is no drawback in supplying it through the same source as the respirator.

The assembly of the warning device according to the invention is housed in a small-sized box, which may be easily fixed to the patient's bed, in the operation room, or in an automobile vehicle.

It will be noted that, by reason of the pressure existing in the sensing tube, the latter does not run the risk of being clogged by the secretions of the patient. It will be noted moreover that, if the rubber of the tracheotomy tubes is of poor quality and does not completely close the orifice, the alarm is given by the device. Finally the device can operate in a caisson : it suffices to increase the supply pressure, so as to maintain a relative pressure of 3 kg/cm$^2$.

Embodiments of a tube disconnection warning device in accordance with the features of the present invention, have been described in the foregoing with regard to its application to respirators. However it must be well understood that it can find applications in connection with all apparatuses operating with fluids, and notably to give warning in the case of disconnection of tubes, pressurised or not, filled with liquids or with gases or any fluids, whatever their temperature, of apparatuses for medical and industrial uses, such as extra-corporal circulating circuits, measuring apparatus circuits of the "Technicon" type for example, chairs for handicapped persons, aeronautical equipment, etc. . . .

I claim:

1. Device for giving warning of the disconnection of a first tube from a second tube, comprising, in combination: first and second tubes having wall surfaces in abutting relationship, a source of gas under pressure, a pneumatic cell of the fully open-fully closed type having an input port, a control port, and first and second output ports, said first output port of said pneumatic cell being pressurized during the presence of pressure in said control port and said second output port of said pneumatic cell being pressurized during the absence of pressure in said control port, said source of gas being connected to said input port of said pneumatic cell, a sensing tube terminating at one end in at least one orifice opening, said opening being positioned between said abutting walls of the first and second tubes when they are normally connected, said sensing tube being connected at its opposite end to said control port of said pneumatic cell, a distributor having first, second, and third input ports and an output port, said first input port of said distributor connected to said source of gas, said second input port of said distributor connected to said first output port of said pneumatic cell, and said third input port of said distributor connected to said second output port of said pneumatic cell, said distributor including means for connecting the first input port and output port thereof in response to pressure in said third output port of said distributor and for disconnecting the first input port and output port thereof in response to pressure in said second input port in said distributor and at least one alarm means connected to the output of said distributor and responsive to pressure therein.

2. The warning device according to claim 1, wherein said first tube is a patient's tubular respirator canula, and said second tube communicates with apparatus for supplying gas to the patient through the canula.

3. The device according to claim 2 wherein said orifice opening is defined by an open end of said sensing tube, said tubular canula and the second tube communicating with the apparatus for supplying gas to the patient, abutting together in coaxial relation, with one tube passing inside the other, with said orifice opening being positioned therebetween.

4. The warning device according to claim 3 wherein said sensing tube comprises a tube entering the canula and terminating in an orifice which is positioned at the outer surface of the canula and against the inner surface of apparatus for supplying gas to the patient.

5. The device according to claim 2 wherein said sensing tube is defined by a tube entering the canula and terminating with said orifice being located at the outer surface of said canula, and positioned against the inner surface of said apparatus for supplying gas to the patient.

6. The warning device according to claim 5 wherein said canula is a branched canula having three open end legs, and a stopper, including two spaced seals, mounted within an open end of one leg of said branched canula, said stopper being adapted for removal therefrom for the aspiration of tracheal secretions, said sensing tube being defined by a tube entering the branched canula comprising three said orifices communicating respectively with the three legs of the canula, one said orifice opening positioned at the outer surface of a first leg of the canula and adapted for positioning against the inner surface of tubular apparatus communicating between the patient and the first leg; a second orifice opening positioned at the outer surface of a second leg of the canula and positioned against the inner surface of a tube, communicating between the canula and a respirator for supplying oxygen; and a third orifice opening communicating with the inner surface of the third stopper-carrying leg of said canula, said opening being positioned between the two seals of the stopper.

7. The warning device according to claim 5 wherein the canula is a branched canula having three openended legs and a stopper, mounted within an open end of one leg of said branched canula, said sensing tube being mounted in said stopper and comprising a tube entering the branched canula and defining two said orifices which open respectively at the outer surfaces of the two legs which do not carry the stopper, one orifice being adapted for opening against the inner surface of tubular apparatus communicating between the patient and with the leg defining said orifice, and one orifice opening at the outer surface of the other said leg and positioned against the inner surface of a tube communicating with said leg and a respirator for supplying oxygen.

8. The device according to claim 2 wherein said respirator canula includes a branched canula defining three open-ended legs, and including a stopper for the aspiration of tracheal secretions positioned to obstruct fluid flow through one said leg, said stopper including two spaced seals, said sensing tube being defined by a tube entering the branched canula and comprising three said orifice openings, each orifice being positioned respectively in a separate leg of said canula, one said orifice opening being adapted for positioning against the inner surface of tubular apparatus communicating with the patient and attached at one end about a first leg of the canula: one said orifice opening being positioned at the outer surface of the second leg of the canula and positioned against the inner surface of said second tube of the respirator, and one said orifice opening being positioned at the inner surface of the third, stopper-carrying leg of the canula, between the two seals of the stopper, said stopper being adapted for removal from the third leg for aspiration of tracheal secretions.

9. The device according to claim 2 wherein said canula is a branched canula having three open-ended legs, one leg being closed with a stopper mounted in an open end of one said leg, said sensing tube being mounted in and passing through said stopper, said sensing tube also including a tube entering said branched canula and defining two orifices which open, respectively, at the outer surfaces of each other leg of said canula, respectively, one orifice opening being adapted for positioning against the inner surface of tubular apparatus communicating with the patient, and one orifice opening being positioned against the inner surface of a tube communicating with a respirator for providing oxygen.

10. The device according to claim 1 comprising a housing constituting a small-sized box to form a compact assembly which can be easily affixed to a patient's bed, or carried in a vehicle.

11. In an oxygen administration device for a patient, a canula defining three open-ended legs, tubular apparatus for communicating with a patient being attached at one end in interface relationship with the outer surface of a first of said legs a tube communicating between a second of said legs and an oxygen source, and being attached at one end in an interface relationship with the outer surface of said second leg a removable stopper being attached in interface relationship with the inner surface of a third of said legs to permit aspiration of tracheal secretions; a branched tube passing through said branched canula including three legs each terminating in an orifice, said orifices of said first and second legs of said branched canula communicating with the outer surfaces of said first and second legs, respectively, and located within the interface of said tubular apparatus and said tube and said first and second legs, respectively, and said orifice of said third leg of said branched canula communicating with an inner surface of said third leg and located within the interface of said third leg and said stopper, said branched tube being connected with pneumatic pressure sensing warning device means which provides a positive pressure to said tube, and activates an alarm means when said positive pressure falls below a predetermined level.

* * * * *